(12) United States Patent
Watanabe

(10) Patent No.: US 8,292,803 B2
(45) Date of Patent: Oct. 23, 2012

(54) ENDOSCOPE

(75) Inventor: Katsushi Watanabe, Hachioji (JP)

(73) Assignee: Olympus Corporation (JP)

( * ) Notice: Subject to any disclaimer, the term of this patent is extended or adjusted under 35 U.S.C. 154(b) by 1226 days.

(21) Appl. No.: 11/367,781

(22) Filed: Mar. 3, 2006

(65) Prior Publication Data

US 2006/0173243 A1    Aug. 3, 2006

Related U.S. Application Data

(63) Continuation of application No. PCT/JP03/11374, filed on Sep. 5, 2003.

(51) Int. Cl.
*A61B 1/00* (2006.01)
(52) U.S. Cl. ........................... 600/142; 600/149
(58) Field of Classification Search ............... 600/139, 600/141, 142, 144, 146, 149, 138, 14, 1, 600/148, 150
See application file for complete search history.

(56) References Cited

U.S. PATENT DOCUMENTS

| | | | |
|---|---|---|---|
| 4,651,718 A | 3/1987 | Collins et al. | |
| 4,686,963 A * | 8/1987 | Cohen et al. | 600/141 |
| 4,700,693 A * | 10/1987 | Lia et al. | 600/141 |
| 4,745,908 A * | 5/1988 | Wardle | 600/139 |
| 4,790,294 A * | 12/1988 | Allred et al. | 600/141 |
| 4,955,384 A * | 9/1990 | Taylor et al. | 600/434 |
| 5,170,775 A * | 12/1992 | Tagami | 356/241.4 |
| 5,271,381 A | 12/1993 | Ailinger et al. | |
| 5,575,753 A * | 11/1996 | Yabe et al. | 600/123 |
| 5,876,330 A * | 3/1999 | Grabover et al. | 600/129 |
| 6,210,337 B1 | 4/2001 | Dunham et al. | |
| 6,364,828 B1 | 4/2002 | Yeung et al. | |
| 6,921,397 B2 * | 7/2005 | Corcoran et al. | 604/535 |
| 7,250,027 B2 * | 7/2007 | Barry | 600/141 |
| 2002/0032371 A1 * | 3/2002 | Torii | 600/142 |

FOREIGN PATENT DOCUMENTS

| | | |
|---|---|---|
| EP | 0 535 847 A1 | 9/1992 |
| EP | 0 782 836 A1 | 7/1997 |
| JP | 60-190301 | 12/1985 |
| JP | 62-192134 | 8/1987 |
| JP | 6-63005 | 3/1994 |

(Continued)

OTHER PUBLICATIONS

International Search Report PCT/JP2003/11374 dated Sep. 25, 2003.

(Continued)

*Primary Examiner* — Anhtuan Nguyen
*Assistant Examiner* — Alireza Nia
(74) *Attorney, Agent, or Firm* — Ostrolenk Faber LLP

(57) ABSTRACT

A slender insertion section of the endoscope has an endoscope distal-end portion, a tubular body and a bending portion, all extending along the longitudinal axis of the insertion section. The bending portion is arranged between the distal-end portion and the tubular body. The insertion section has an inner component. The bending portion has an annular ring assembly composed of a plurality of annular rings arranged side by side. Each annular ring has a ring body, a pair of bulging portion that face at one end face of the ring body, and a plurality of projections which the inner component can move. The most distal annular ring of the annular ring assembly supports one end of a wire. The wire passes through the annular rings and has its other end coupled to an operation section of the endoscope.

6 Claims, 12 Drawing Sheets

FOREIGN PATENT DOCUMENTS

| | | |
|---|---|---|
| JP | 2001-46322 | 6/1999 |
| JP | 2000-296103 A | 10/2000 |
| JP | 2002-320587 | 11/2002 |
| JP | 2003-260020 | 9/2003 |

OTHER PUBLICATIONS

Search Report issued by European Patent Office in connection with corresponding application No. EP 03 81 8581 on May 25, 2010.

* cited by examiner

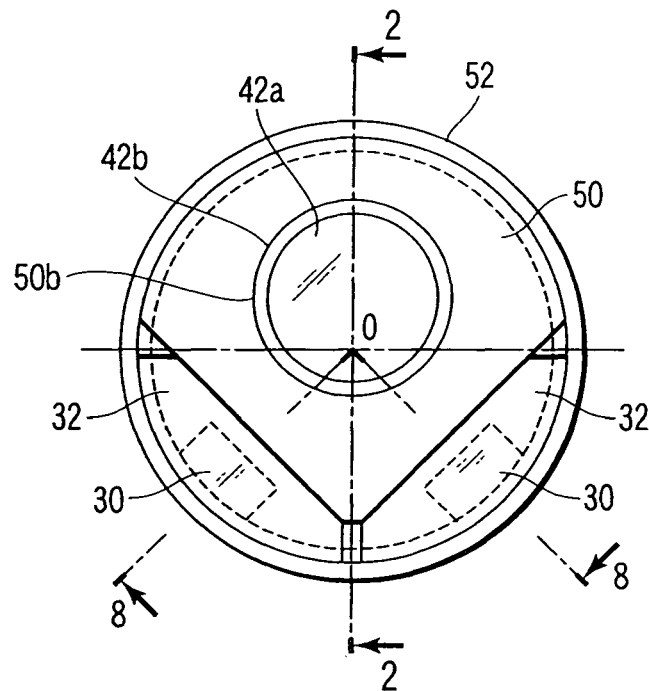
F I G. 3
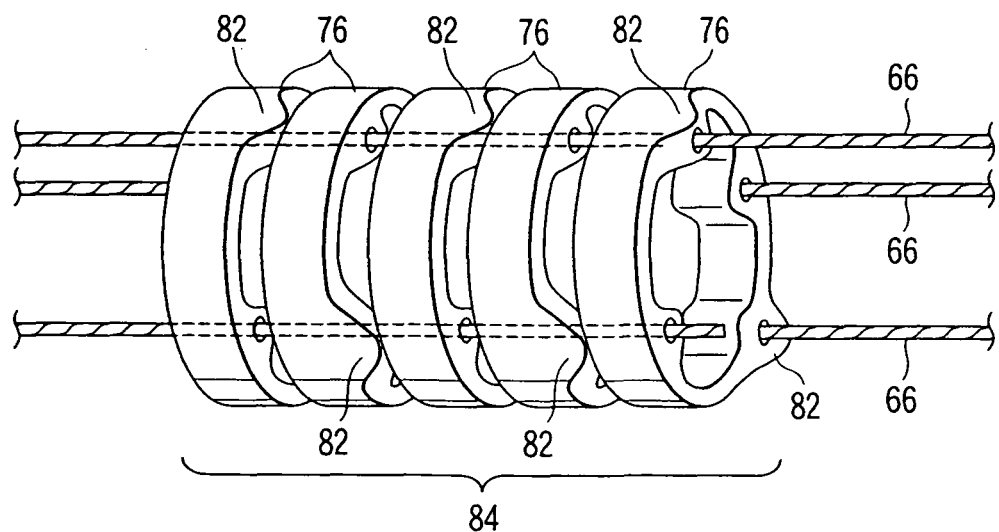
F I G. 4

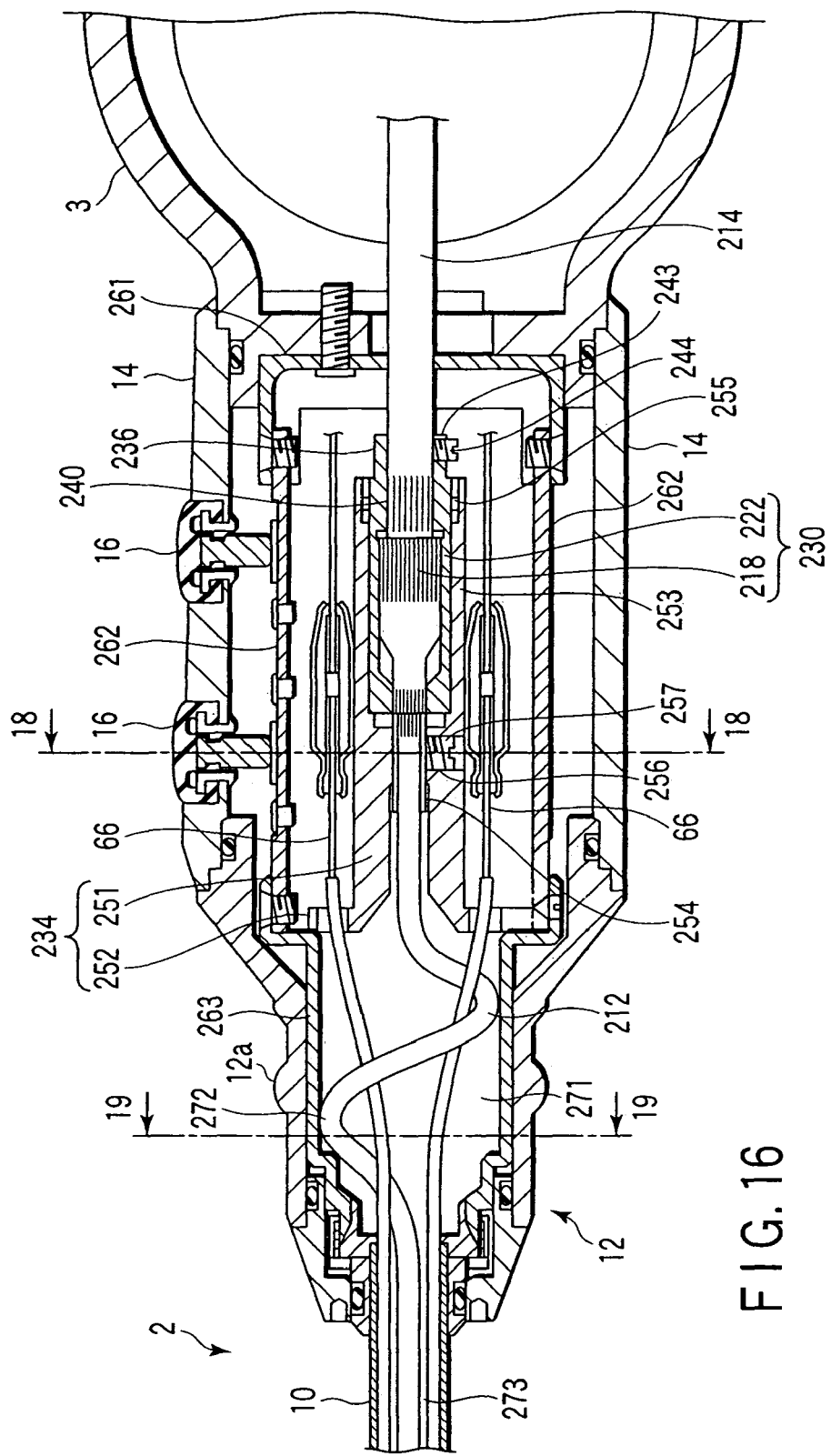
F I G. 16

ENDOSCOPE

CROSS-REFERENCE TO RELATED APPLICATIONS

This is a Continuation Application of PCT Application No. PCT/JP03/11374, filed Sep. 5, 2003, which was published under PCT Article 21(2) in Japanese.

BACKGROUND OF THE INVENTION

1. Field of the Invention

The present invention relates to an endoscope having, at the distal end of the insertion section, a bending portion that can be bent.

2. Description of the Related Art

Endoscopes are used in medical treatment and industry. The endoscope designed for medical treatment has an elongated insertion section, which is inserted into the body cavity so that the tissues and organs in the cavity may be observed. The endoscope designed for industrial use is widely used in laying pipes and tubes in boilers, gas-turbine engines and chemical plants and in inspecting the interior of, for example, automobile engines to detect damages and corroded parts.

Most endoscopes of this type have a bending portion at the distal end of the insertion section that is to be inserted into the lumen. The bending portion can be bent. It includes a plurality of annular ring (bending segments) that are arranged in series along the axis of the insertion section. The annular rings are coupled to one another with rivets. Each annular ring is able to rotate for the adjacent annular ring. Each annular ring is a hollow member and has wire guides, which protrude inwards in the radial direction of the annular ring. Traction wires pass through the wire guides, respectively. The operation section, i.e., the proximal end of the endoscope, incorporates a bending-operation mechanism. The traction wires are coupled to the bending-operation mechanism. More precisely, the wires are connected to a bending knob provided in the bending-operation mechanism. When the bending knob is turned, the traction wires are pulled at one end, bending the bending portion upwards, downwards, leftwards or rightwards.

Jpn. Pat. Appln. KOKAI Publication No. 62-192134, for example, discloses an endoscope having a bending portion whose annular rings have a hollow with an increased sectional area. Each annular ring has wire guides that indeed lie in the hollow but do not contact the heads of the rivet. The projection protruding into the hollow of each annular ring is made as small as possible. This provides room for components and making it possible to reduce the outer diameter of the annular rings.

Jpn. UM Appln. KOKAI Publication No. 60-190301 discloses an endoscope having a bending portion. In this bending portion, the rivets coupling the annular rings (bending tubes) extend outwards in the radial direction of the insertion section. Therefore, the heads of the rivets do not project inwards in the radial direction of the annular rings. The component density is thus high in each annular ring.

Jpn. Pat. Appln. KOKAI Publication No. 2000-296103 discloses an endoscope having a bending portion. The bending portion includes a plurality of annular rings that are arranged in series along the axis of the insertion section. Each annular ring has wire guides and a bulging part that works as a rotation fulcrum. Traction wires pass the wire guides, respectively. The bulging part abuts on the next annular ring, coupling the annular ring to the next annular ring. Thus, no rivets are used to couple the annular rings. Since fastening parts, such as rivet heads project outwards or inwards of the annular ring, need not be used at all, the insertion section can be greatly reduced in diameter and the component density can be high. As a result, an endoscope having an insertion section of a small diameter can be provided.

BRIEF SUMMARY OF THE INVENTION

An endoscope includes an operation section which is to be operated by a surgeon, and an insertion section which has a distal end, a proximal end and a longitudinal axis, which is connected at the proximal end to the operation section. The insertion section has an endoscope distal-end portion which is provided at the distal end of the insertion section, a tubular body which is provided between the endoscope distal-end portion and the operation section, a bending portion which is provided between the endoscope distal-end portion and the tubular body, an inner component having flexibility, and at least one wire which is coupled at the other end to the operation section and is operated to bend the bending portion. The bending portion has an annular ring assembly including a plurality of annular rings arranged along the longitudinal axis of the insertion section. Each annular ring includes a ring body which has two end faces opposing each other, a pair of bulging part which face at one of the end faces, which oppose to each other and which function as fulcrums for an adjacent annular ring, a plurality of projections which are formed integral with the annular ring and protrude toward a center of the ring body and which define spaces, and at least one through hole which penetrates the two end faces of the ring body. The inner component is secured at one end to the endoscope distal-end portion, extends along the longitudinal axis toward the proximal end of the insertion section, passes along the longitudinal axis through the bending portion. The inner component is able to move in the spaces while passing through the annular rings. The wire is supported at one end by the annular ring closest to the distal end of the insertion section, passes through the through hole of each annular ring.

BRIEF SUMMARY OF THE INVENTION

FIG. 3 is a schematic front view depicting the distal-end portion of the insertion section of the endoscope according to the first embodiment;

FIG. 4 is a schematic perspective view showing how the annular rings are arranged in the insertion section of the endoscope according to the first embodiment;

FIG. 16 is a longitudinal sectional view of the operation section of an endoscope according to a third embodiment;

Figure 18:
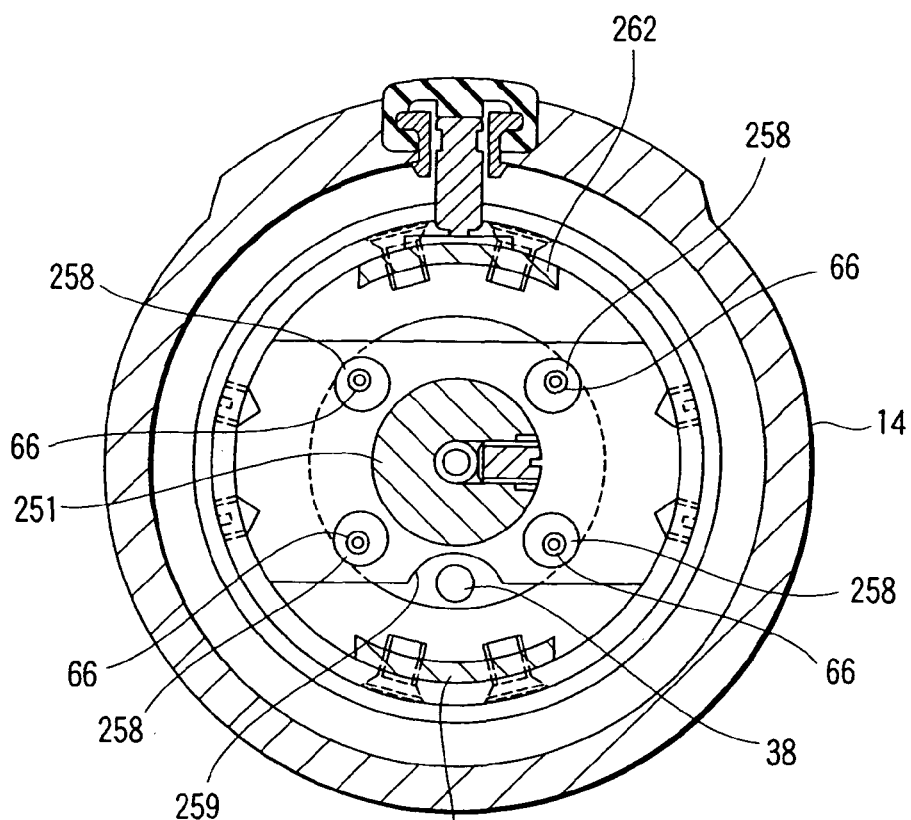
Figure 19:
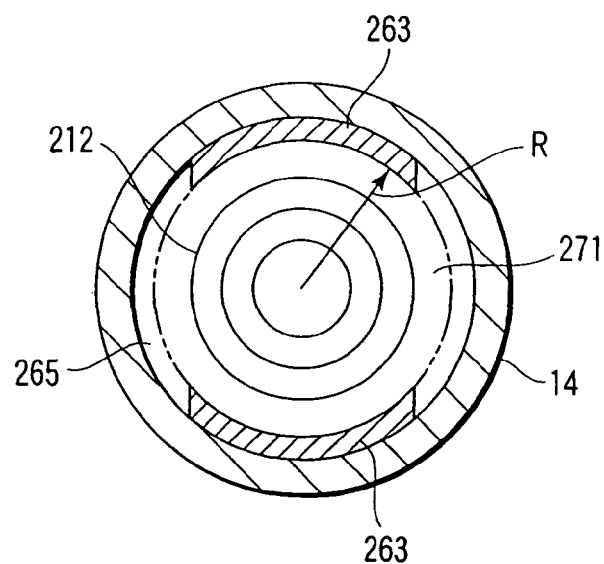

FIG. 18 is a sectional view of the operation section of the endoscope scope according to the third embodiment, taken along line 18-18 shown in FIG. 16; and FIG. 19 is a schematic sectional view taken along line 19-19 shown in FIG. 16, showing the support member and tubular body provided in the operation section of the endoscope according to the third embodiment, the tubular body containing light-guide glass fibers.

DETAILED DESCRIPTION OF THE INVENTION

Some of the best modes for carrying out this invention (hereinafter called embodiments) will be described, with reference to the accompanying drawings.

A first embodiment will be described, with reference to FIGS. 1 to 6.

Figure 1:
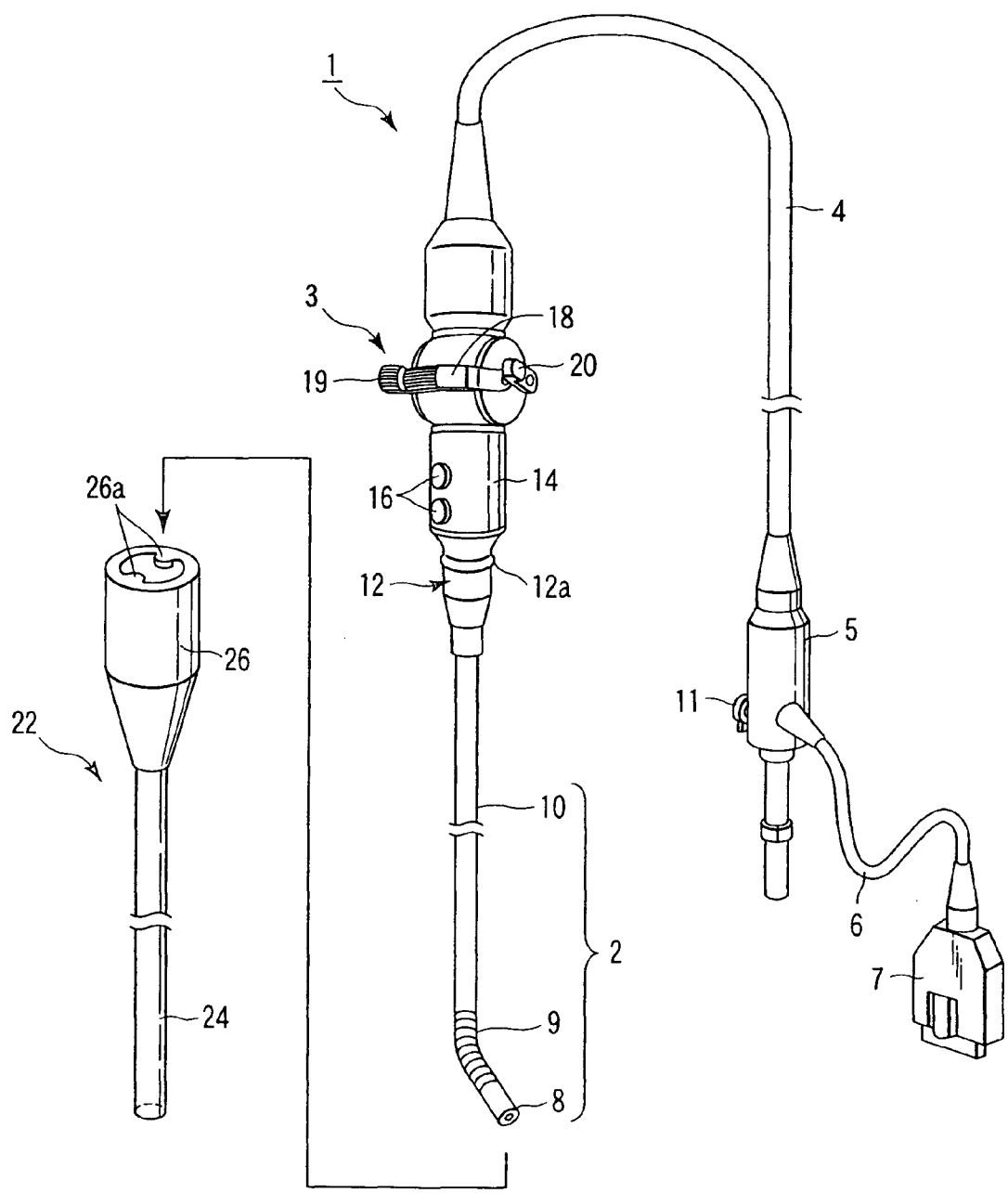
FIG. 1 is a schematic perspective view showing a preferred endoscope according to a first embodiment.

As FIG. 1 shows, the endoscope 1 according to the present embodiment includes an endoscope insertion section 2 and an endoscope operation section 3. The insertion section 2 is an elongated unit. The operation section 3 is connected to the proximal end of the insertion section 2. To the proximal end of the operation section 3, a universal cable 4 is connected at one end, for applying illumination light from a light-source apparatus (not shown) and transmitting various signals. A light guide connector 5, to which the light-source apparatus is connected, is provided at the other end of the universal cable 4.

A camera cable 6 extends, at one end, from the circumference of the light guide connector 5. To the other end of the camera cable 6 there is connected a camera connector 7, to which a CCU (not shown) is connected.

A monitor is connected to the CCU. When a solid-state imaging element such as a CCD element photographs an object to be examined, generating a video signal representing the image of the object, the CCU processes the signal and supplies it to the monitor. The monitor displays the image of the object photographed.

The light guide connector 5 has an air-inlet cap 11 in its circumferential surface. The air-inlet cap 11 is used to inspect the endoscope 1 for water leakage (watertight condition). Air is supplied through the air-inlet cap 11 into the endoscope 1. The endoscope 1 is then immersed in water, to see whether bubbles come from the endoscope 1 (or to determine whether the water may leak from the endoscope 1). The air-inlet cap 11 can be opened to connect the interior of the endoscope 1 to with the outside and be closed to disconnect the interior of the endoscope 1 from the outside. The cap 11 usually remains closed, rendering the endoscope 1 watertight, not allowing water (liquid) from entering the endoscope 1.

The insertion section 2 includes an endoscope distal-end portion 8, a bending portion 9, and a rigid portion 10. The endoscope distal-end portion 8 is hard. The bending portion 9 can bend upwards and downwards, and leftwards and rightwards. The rigid portion 10 is a pipe that is hard and long. The endoscope distal-end portion 8 is located at the distal end of the endoscope insertion section 2. The bending portion 9 is coupled at the distal end to the proximal end of the endoscope distal-end portion 8. The hard part 10 is coupled at the distal end to the proximal end of the bending portion 9. The hard part 10 is made of hard metal such as stainless steel. The endoscope operation unit 3 is coupled at the distal end to the proximal end of the hard part 10. In other words, the distal end of the operation section 3 is coupled to the proximal end of the insertion section 2.

At the distal end of the operation section 3, a support member 12 is provided, supporting the proximal end of the rigid portion 10. The support member 12 has a distal end part that is tapered, gradually narrower toward the proximal end of the rigid portion 10. An annular projection 12a protruding outward in the radial direction is integrally formed with the outer circumference of the support member 12. A grip 14, which the operator may hold, is provided at the proximal end of the support member 12. The grip 14 has an image storage device (not shown) e.g. VTR or the like, and remote switches 16 that control, when operated, a camera control unit (not shown, hereinafter referred to as CCU).

Bending levers 18 and 19 are provided on the proximal end of the grip 14. When the operator operates these levers 18 and 19, the bending portion 9 is bent, deviating from the axis of the rigid portion 10. For example, the bending portion 9 is bend upwards and downwards, and leftwards and rightwards.

A holding lever 20 is provided besides the bending lever 18. When operated, the holding lever 20 holds the bending lever 18 at a desired position, ultimately holding the bending portion 9 in a desired bent state. Another holding lever (not shown) is provided beside the other bending lever 19.

The insertion section 2 of the endoscope 1 thus configured is used, covered with a protective sheath 22 that protects mainly the bending portion 9. The protective sheath 22 includes a sheath part 24 and a proximal part 26. The sheath part 24 is a tubular member that is highly flexible. The proximal part 26 is connected to the proximal end of the sheath part 24. The proximal part 26 has an opening. A pair of engagement projections 26a, for example, are formed on the inner wall of the proximal part 26. As the distal-end portion 8 of the endoscope insertion section 2 is gradually inserted into the protective sheath 22 from the opening of ht proximal part 26, the engagement projections 26a move over the annular projection 12a of the support member 12 and are engaged with the support member 12. The protective sheath 22 can be detached from the outer circumference of the endoscope insertion section 2.

The distal-end portion 8, bending portion 9 and rigid portion 10 of the insertion section 2 will be described in terms of internal structure, with reference to FIGS. 2 to 6.

Figure 2:
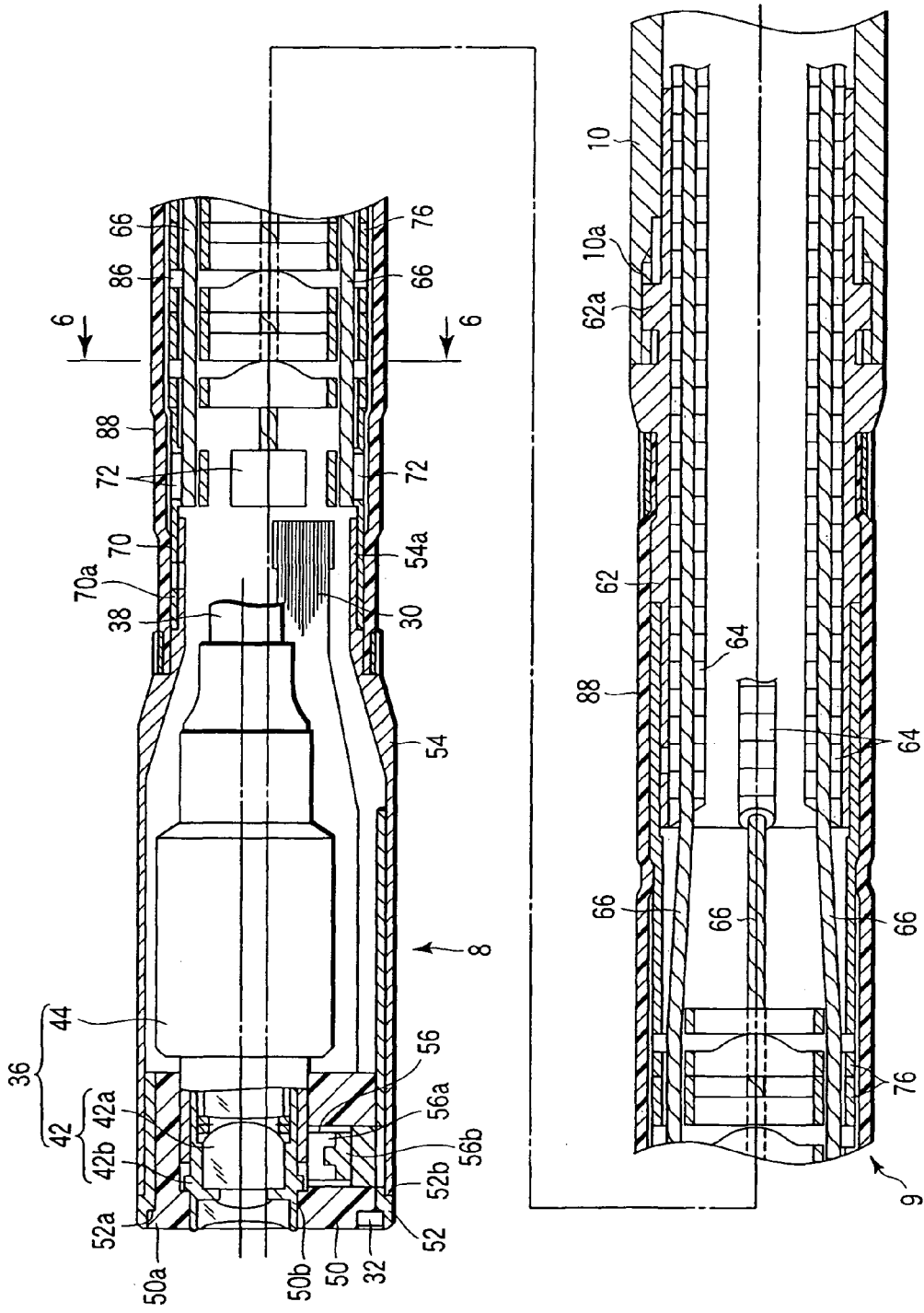
FIG. 2 is a schematic, longitudinal sectional view of the distal-end portion of the insertion section of the endoscope according to the first embodiment.

As FIG. 2 shows, the insertion section 2 of the endoscope 1 according to this embodiment incorporates an illumination optical system and an objective optical system.

The illumination optical system includes light guides 30 and illumination windows 32. More precisely, a pair of light guides 30 and a pair of illumination windows 32 are provided. The light guides 30 guide illumination light, which illuminates the objects that exists in a body cavity and are to be examined. The illumination windows 32 apply the illumination light guided by the light guides 30, to the objects. The windows 32 are, for example, flat glass plates. The illumination windows 32 are secured to the distal-end face of the main body 50 of the distal-end portion 8. The main body 50 will be described later.

The light guides 30 are, for example, light-guide fiber bundles. The end portions of each light guide 30 has a specific sectional shape defined by bonding the fibers together with an adhesive or the like. The portion of each light guide 30, other than the end portions, can change in sectional shape.

The two light guides 30 extend from the proximal end of the endoscope insertion section 2, pass through the operation section 3 and are led into the universal cable 4. The light guides 30 are connected at proximal end to the light guide connector 5. The light guide connector 5 is connected to the light-source apparatus. Hence, the illumination light emitted from the light-source apparatus travels through the light guide connector 5 to the distal ends of the light guides 30, and is applied from the illumination windows 32.

The objective optical system of the insertion section 2 includes an imaging unit 36 and an imaging cable 38. The imaging unit 36 has an objective-lens system 42 and an imaging section 44.

The objective-lens system 42 has a lens assembly 42a and a lens barrel 42b. The lens assembly 42a constitute a combination lens. The lens barrel 42b is made of metal and holds the lens assembly 42a. The lens assembly 42a guide an optical image of an object illuminated with the illumination light and images the image on a solid-state imaging element, which will be described later.

The imaging section 44 incorporates a solid-state imaging element such as a CCD element. The solid-state imaging element is electrically connected to the imaging cable 38, via an electronic circuit board (not shown) that is provided in the imaging section 44. Like the light guides 30, the imaging cable 38 extends from the proximal end of the endoscope insertion section 2, pass through the operation section 3 and are led into the universal cable 4. The imaging cable 38 is coupled at proximal end to the light guide connector 5. The light guide connector 5 is connected to a video processor or the like, by the camera cable 6 and the camera connector 7.

When the image of an object illuminated with the illumination light is applied to the objective-lens system 42, it is imaged on the solid-state imaging element provided in the imaging section 44. The imaging element generates a video signal that represents this image. The video signal is input to the video processor through the imaging cable 38, operation section 3, universal cable 4, light guide connector 5, camera cable 6 and camera connector 7.

As FIG. 2 depicts, the distal-end portion 8 includes a main body 50, a distal-end barrel 52, and a cylindrical member 54. The distal-end barrel 52 is a hollow cylindrical member and mounted on the main body 50. The cylindrical member 54 is substantially a hollow cylinder and mounted on the distal-end barrel 52, functioning as sheath to the barrel 52.

The main body 50 is made of insulating material such as resin (plastics) or ceramics. A flange 50a is integrally formed with the distal-end portion 8 of the main body 50. The main body 50 has an objective-system holding hole 50b made in the center part. The objective-system holding hole 50b has a longitudinal axis that is aligned with the longitudinal axis of the insertion section 2. The lens barrel 42b of the imaging unit 36 provided in the objective optical system is fitted in the objective-system holding hole 50b, sealed watertight to the main body 50.

As FIG. 2 shows, the main body 50 has a screw hold 56 that opens to the objective-system holding hole 50b. The screw hole 56 extends at right angles to the longitudinal axis of the objective-system holding hole 50b. A screw 56a is driven from the outer circumference of the lens barrel 42b and set in engagement with the screw hole 56. The lens barrel 42b of the imaging unit 36 is thereby fastened to the main body 50. The screw hole 56 is filled with filling material 56b, which holds the screw 56a firmly held in the hole 56 and keeps sealing the lens barrel 42b watertight to the main body 50.

The distal-end barrel 52 is a thin-walled round tube made of metal. As FIG. 2 depicts, the distal-end barrel 52 has a stepped part 52a in the inner surface. The flange 50a of the main body 50 abuts on the stepped part 52a. The distal-end barrel 52 has a stepped part 52b in the outer surface. The distal end of the cylindrical member 54 abuts on the stepped part 52b.

The cylindrical member 54 is, for example, a thin-walled round tube made of metal such as stainless steel. The proximal end part of the cylindrical member 54 has a smaller diameter than the distal end part; it is a small-diameter part 54a having a stepped part.

As FIGS. 2 and 3 show, the distal-end barrel 52 is fitted in the distal end of the cylindrical member 54 and secured thereto by bonding. In the distal-end barrel 52, the flange 50a of the main body 50 abuts on the stepped part 52a. The flange 50a and the stepped part 52a are fastened to each other by bonding. As a result, the main body 50 and the stepped part 52b are firmly bonded together, forming a single unit. The distal-end portion 8 of the endoscope insertion section 2, which is composed of the main body 50 and stepped part 52b, has a distal-end face that is almost flat and extends at right angles to the longitudinal axis of the insertion section 2.

As FIGS. 2 and 3 show, the main body 50 and stepped part 52b define a space when they are fastened to each other. The distal end parts of the light guides 30 are arranged in this space. The distal end parts of the light guides 30 have a rectangular cross section. The illumination windows 32 are attached to the light guides 30, respectively. The illumination windows 32 are secured to the main body 50 with transparent adhesive or the like, in watertight fashion.

The rigid portion 10 of the insertion section 2 will be described, with reference to FIG. 2.

As shown in FIG. 2, a female screw 10a is cut in the inner circumferential surface of the distal end of the rigid portion 10. A cap 62, which is a hollow cylinder, is mounted on the proximal end part of the bending portion 9 and secured thereto by bonding. The cap 62 has a male screw 62a in the outer circumferential surface. The male screw 62a is set in engagement with the female screw 10a. Thus, the bending portion 9 and the rigid portion 10 are connected and fastened to each other.

As FIG. 2 depicts, four coil sheaths 64, independent of each other, are inserted in the rigid portion 10. A traction wire 66 extends through each coil sheath 64.

The coil sheaths 64 are secured at distal end to the cap 62 provided at the distal end of the bending portion 9, with silver solder or solder. Wrapping the coil sheaths 64, respectively, the traction wires 66 would not damage the components such as the light guides 30 and the imaging cable 38, as they are moved back and forth in the rigid portion 10.

The configuration of the endoscope bending portion 9 will be described, with reference to FIGS. 2, and 4 to 6.

A cap 70 is provided at the distal end of the endoscope bending portion 9. One of the annular rings 76, which is closer to the distal-end portion 8 than any other, is secured to the proximal end of the cap 70, by means of, for example, bonding. The cap 70 has a connecting part 70a, or a distal end part. The connecting part 70 is mounted on the distal-end portion 8. More precisely, the connecting part 70a abuts on the outer circumferential surface of the small-diameter part 54a of the cylindrical member 54 and is secured to the part 54a by bonding. A wire-holding part 72 is provided on the inner surface of that part of the cap 70, which is more proximal than the connecting part 70a. The wire-holding part 72 holds the distal ends of the traction wires 66. Silver solder, for example, is applied, securing the traction wires 66 to the wire-holding part 72.

The coil sheaths 64 and traction wires 66 have their proximal ends fitted in the holding member (not shown) of a bending-operation mechanism, in the vicinity of the endoscope operation section 3. The traction wires 66 are therefore coupled at proximal end to the bending-operation mechanism. More precisely, the traction wires 66 of the one pair are connected to the bending lever 18, and the traction wires 66 of the other pair to the bending lever 19. Thus, the traction wires 66 of the first pair are pulled and slackened when the bending lever 18 is rotated, and the traction wires 66 of the second pair are pulled and slackened when the bending lever 19 is rotated.

Figure 5:
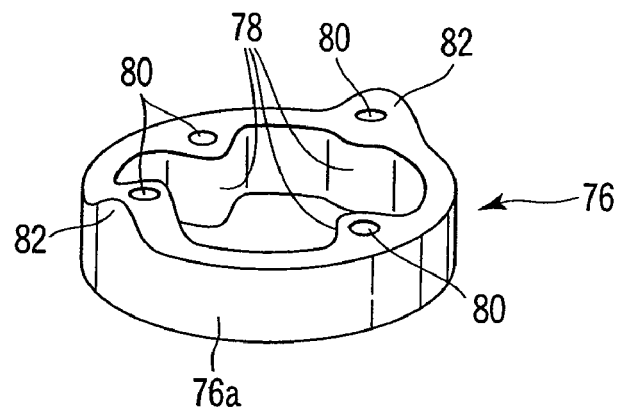
FIG. 5 is a schematic perspective view of one of the annular rings provided in the endoscope according to the first embodiment.

In the bending portion 9, the annular rings 76 are arranged in a row, along the longitudinal axis of the endoscope insertion section 2, as is illustrated in FIG. 2 and FIG. 4. As FIG. 5 shows, each tubular body 76 is shaped like a ring. The ring body 76a of the tubular body 76 is almost uniform in thickness as measured along the longitudinal axis, except bulging parts 82 which will be described later. The front and back of the tubular body 76, with respect to the longitudinal axis, are almost flat.

Projections 78 are integrally formed with the ring body 76a. They protrude inwards in the radial direction of the tubular body 76. The projections 78 are arranged along the circumference of the tubular body 76, equidistantly spaced by angular distance of about 90°. The projections 78 have a wire-guiding hole (wire-guiding portion) 80 each, which is located in a circle substantially aligns with the inner circumference of the annular ring 76. The traction wires 66 extend through the four wire-guiding holes 80 of the annular ring 76, respectively, and can move back and forth in the direction of thickness of the annular ring 76. The wires 66 pass through the wire-guiding holes 80, extending straight at right angles to the front and back of the annular ring 76.

As FIG. 4 and FIG. 5 show, two of the four projections 78, the two that oppose with respect to the axis of the annular ring 76 have a bulging portion 82 on only one side of the body 76. The bulging parts 82 are shaped like an arc, protruding along the longitudinal axis of the annular ring 76. They function as fulcrums of rotation for the adjacent annular ring 75.

The annular rings 76 are so arranged that the bulging parts 82 of one body 76 face the that side of the next body 76 which has no bulging parts 82. Of any two annular rings 76 adjacent to each other, one is rotated by 90° with respect to the other. Hence, the bulging parts 82 of one body 76 abut on that side of the other body 76 which has no projections. The annular rings 76 are thus arranged, forming an annular ring assembly 84.

The bending portion 9 may be designed to bend upwards and downwards, and leftwards and rightwards, at various angles. In this case, any two adjacent annular rings 76 need not be so arranged that one is rotated by 90° around its axis with respect to the other. The adjacent bodies 76 can take the same position.

The annular rings 76 are made of stainless steel such as SUS303 or SUS304. The bodies 76 have been machined by, for example, cutting. Alternatively, the bodies 76 may be made by means of metal injection molding. They may be formed by processing powder of stainless steel such as SUS303, SUS304, SUS316, SUS630 or the like.

As can be seen from FIG. 2, the annular ring assembly 84 is the bone structure of the bending portion 9. The annular ring assembly 84 is covered with a mesh tube 86 that can be bent. The mesh tube 86 is in turned covered with a flexible tube 88 that can be easily bent.

As FIGS. 2 and. 6 depict, the two light guides 30 and the imaging cable 38 extend through the annular ring assembly 84 of the bending portion 9. The light guides 30, the imaging unit 36 and the other components have their proximal ends fixed at prescribed positions in the distal-end portion 8 of the endoscope insertion section 2. As a result, the components, including the light guides 30 and imaging unit 36, assumes specific positions in the bending portion 9.

The gaps between the projections 78 of the annular rings 76 define four component-accommodating spaces (receptacle) 90. The projections 78 serve as partitions that suppress the interference between the light guides 30, or as an interference-suppressing mechanism.

In two adjacent component-accommodating spaces 90, two light guides 30 having flexibility are arranged, respectively, sufficiently spaced apart from the inner circumferential surfaces of the annular rings 76. A space remains between each light guide 30 and the inner circumferential surface of each annular ring 76. Each light guide 30 can therefore move in the space 90, prevented from slipping out of the space 90. This suppresses the interference between the light guide 30 and each annular ring 76.

An imaginary circle 92 is inscribed about the apices of the four projections 78 of each tubular body 76. The imaging cable 38 having comparatively high flexibility is provided in the imaginary circle 92, sufficiently spaced from the inner circumferential surface of each annular ring 76. Thus, the interference between the imaging cable 38 and each annular ring 76 is suppressed.

The flexible components 30 (light guides) are thus arranged (provided) in the component-accommodating spaces 90 described above. The greatly flexible component 38 (imaging cable) is arranged (provided) within the imaginary circle 92.

The endoscope may be of the type in which optical images are transmitted by image guide fibers. In this case, the image guide fibers (30a, FIG. 6) are arranged in the component-accommodating spaces 90. The endoscope may otherwise be of the type that has a forceps channel through which an instrument, such as a forceps, extends. If this is the case, the forceps channel (30b, FIG. 6) is arranged within the imaginary circle 92.

How the operation section 3 of the endoscope 1 is operated to bend the bending portion 9 in a desired direction, thereby to observe an object, will be described with reference to the drawings.

Figure 6:
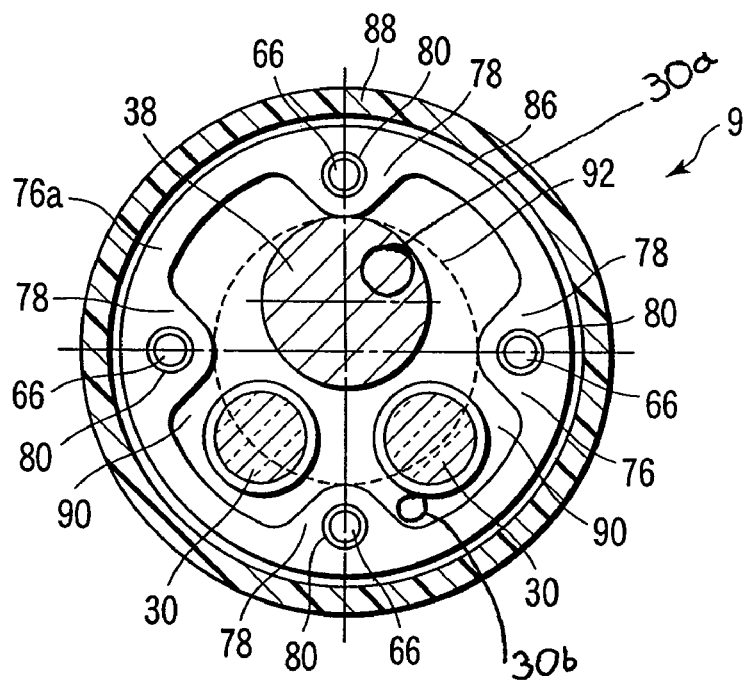
FIG. 6 is a sectional view of the endoscope according to the first embodiment, taken along line 6-6 shown in FIG. 2.

The operator may rotate the bending levers 18 and 19 provided on the proximal end of the endoscope operation section 3 shown in FIG. 1, pulling two pairs of tracking wires 66 shown in FIGS. 4 and 6, in a desired direction, or toward the operation section 3. The annular rings 76 provided in the distal-end part are thereby inclined. As a result, a rotation moment is generated in the direction the traction wires 66 are pulled. The rotation moment rotates each annular ring 76, with the apex of the bulging portion 82 functioning as fulcrum. The annular rings 76 are rotated, one after another. The bending portion 9 is therefore bent as a whole, in the direction the bending levers 18 and 19 have been rotated.

The part near the distal-end portion 8 may be held while the object is being observed or washed. Alternatively, the motion of the distal-end portion 8 may be restricted for some reason. In either case, the insertion section 3 may be rotated around the longitudinal axis of the insertion section 2. How the insertion section 3 is so rotated will be explained below.

The operation section 3 is thus rotated (or twisted) around the longitudinal axis of the insertion section 2, while the distal-end portion 8 remains hardly movable. Then, the twisting force is transmitted to the bending portion 9 provided at the distal end of the rigid portion 10 that is integrally formed with the operation section 3. The annular ring assembly 84 is therefore twisted, whereby the bending portion 9 is twisted in its entirety.

When the annular ring assembly 84 receives the twisting force, all annular rings 76, but the annular ring 76 closest to the distal-end portion 8, rotate sequentially toward the proximal end of the bending portion 9, while the closest tubular body 76 functioning as fulcrum. As a result, the component-accommodating spaces 90 (and projections 78) provided in each annular ring 76 move, describing spiral loci that are substantially spiral. As indicated above, the light guides 30 are secured to the distal-end portion 8. Therefore, the light guides 30 are twisted as they move through the spiral paths defined by the component-accommodating spaces 90 provided in the annular rings 76. The light guides 30 lie sufficiently loose in the component-accommodating spaces 90. The projections 78 of each tubular body 76 of each annular ring 76 extend inwardly in the radial direction thereof, and a space is provided between each light guide 30 and the inner circumferential surface of the ring body 76a of each annular ring 76. Hence, each light guide 30 moves, narrowing the gap between it and the ring body 76a. This prevents the light guides 30 of one pair, lying in two adjacent component-accommodating spaces 90, from moving into the adjacent component-accommodating spaces 90 in which the light guides 30 of the other pair are accommodated. Namely, the light guides 30 of one pair would not interfere with those of the other pair.

The imaging cable 38 is arranged within the imaginary circle 92 that is inscribed about the apices of the four projections 78. Since the imaging cable 38 is fixed at the distal-end portion 8, it is twisted within the imaginary circle 92 as the operation section 3 is rotated. The interference between the apices of the four projections 78 and the imaging cable 38 is suppressed even if the bending portion 9 is twisted.

The annular ring assembly 84 assumes an almost spiral shape, and the light guides 30 move through the component-accommodating spaces 90. Then, the imaging cable 38 moves, remaining within the imaginary circle 92, through a spiral path as the light guides 30 move through spiral paths. This also suppresses the interference between the light guides 30 and the imaging cable 38.

As can be understood from the foregoing, this embodiment is advantageous in the following respects.

The bundles of flexible components, such as the light guides 30, are arranged in the component-accommodating spaces 90 that lie between the adjacent projections 78. Therefore, the spaces 90 can remain sufficiently large even if the bending portion 9 is twisted. In addition, the interference between the adjacent components 30 can be suppressed, because the apices of the projections 78 restrict the motion of the components (light guides) 30 that lie in the component-accommodating spaces 90.

As described above, the components having high flexibility, such as the imaging cable 38, are arranged within the imaginary circle 92 that is inscribed about the apices of the four projections 78. Thus, the projections 78 will not directly interfere with the component (imaging cable) 38 even if the bending portion 9 is twisted. The component 38 can therefore lie sufficiently loose in the bending portion 9, and extend through the bending portion 9 twisted. This reduces the possibility that the components 30 and 38 are disconnected from the distal-end portion 8 of the insertion section 2 when they are pulled as the bending portion 9 is twisted.

The bending portion 9 of the endoscope 1 according to the present embodiment has no mechanical coupling structure. The bending portion 9 is rich in flexibility as a whole. When the distal-end portion 8 receives an external force unexpectedly, no stress is concentrated in it.

The present embodiment can therefore provide an endoscope 1 including the bending portion 9 that has a small outer diameter and contains components 30 and 38 packed densely. Even if the bending portion 9 is twisted, the components 30 and 38 lie within the imaginary circle 92 and remain loose in the spaces 90 provided in the bending portion 9. This can suppress the interference between the components 30 and the component 38, and the interference between the components 30 and 38 and the annular rings 76 of the bending portion 9.

Thus, in the endoscope 1 according to this embodiment, the interference between the components 30 and 38 that extend in the endoscope bending portion 9 and the annular rings 76 and/or the interference between the components 30 and the component 38.

A second embodiment of this invention will be described, with reference to FIGS. 7 to 15. This embodiment is a modification of the first embodiment. The components identical to those of the first embodiment are designated at the same reference numerals and will not be described in detail.

Figure 7:
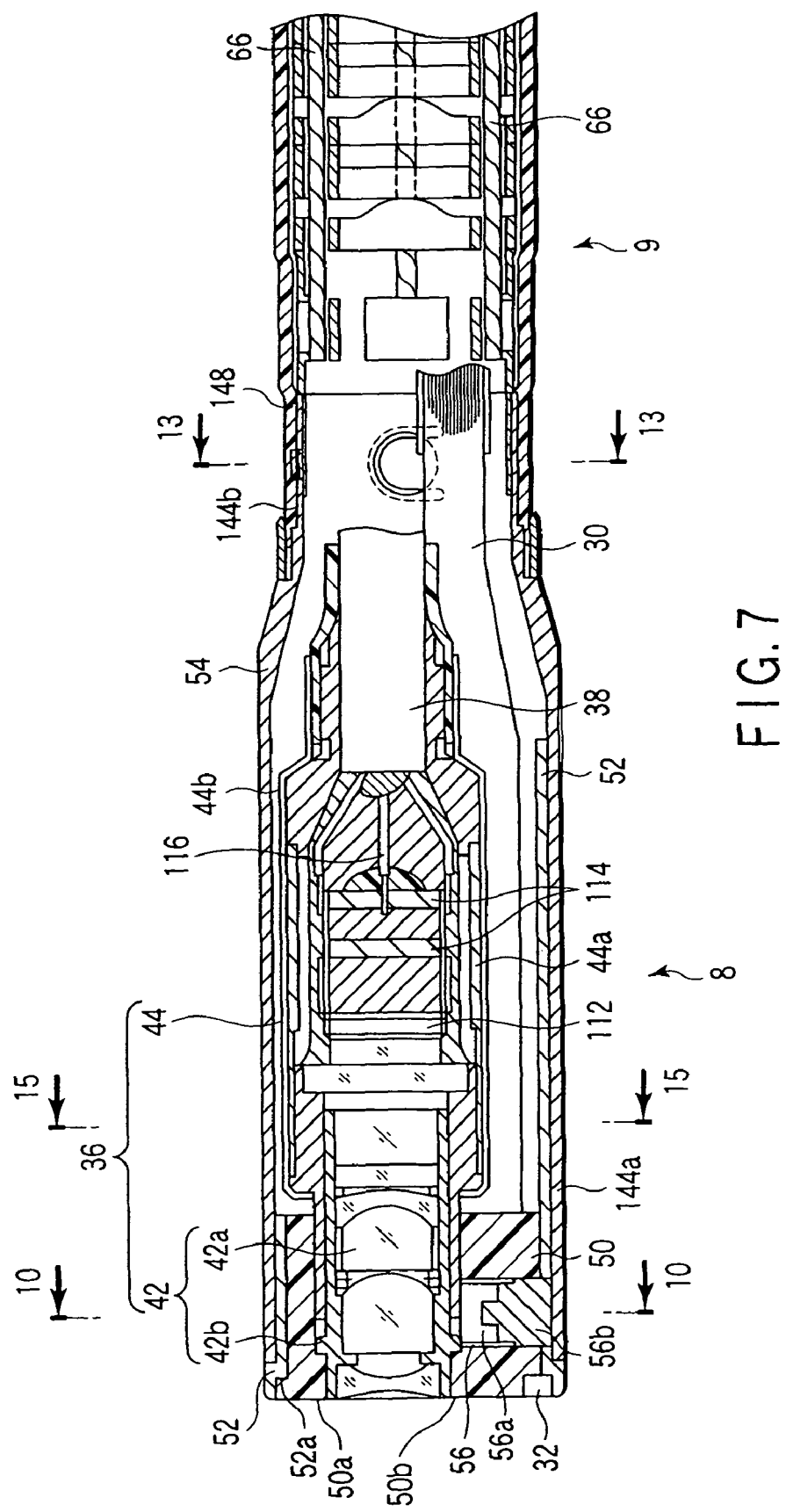
FIG. 7 is a schematic, longitudinal sectional view showing the distal-end portion of the insertion section of the endoscope according to a second embodiment.
Figure 8:
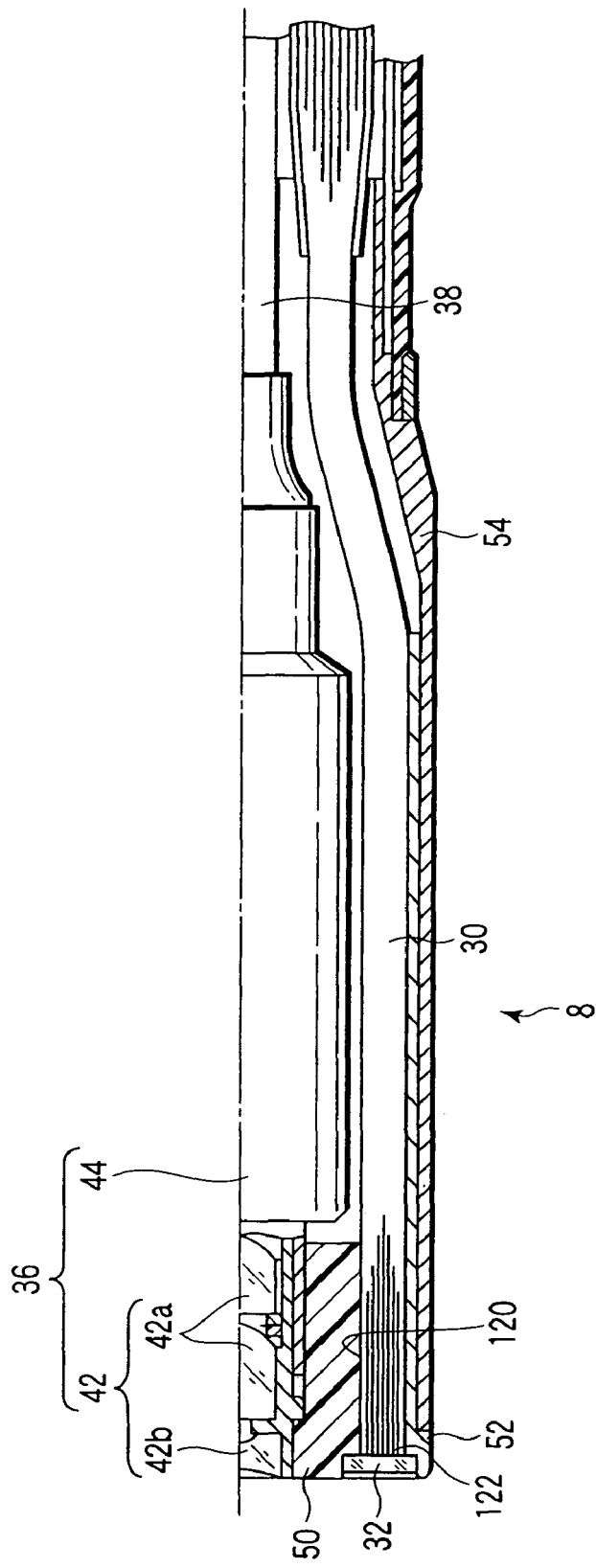
FIG. 8 is a sectional view of the endoscope according to the second embodiment, taken along line 8-0-8 shown in FIG. 3.

As FIGS. 3, 7 and 8 show, the light guides 30 and the imaging unit 36 are secured to the main body 50 of the endoscope distal-end portion 8.

As shown in FIG. 7, the imaging section 44 is provided in a hollow cylindrical member 44a. This member 44a is made of metal and has a small wall thickness. Thus, the imaging section 44 has a smaller outer diameter than the cylindrical member 44a and is reinforced by the cylindrical member 44a to a particular strength. The hollow cylindrical member 44a is covered, at its outer circumferential surface, with an electrically insulating tube 44b that is made of, for example, resin. The tube 44b therefore electrically insulates the outer circumferential surface of the imaging section 44 from the cylindrical member 54 (i.e., outer sheath).

The imaging section 44 incorporates a solid-state imaging element 112 such as a CCD element. An electronic circuit board 114 is provided at the back of the solid-state imaging element 112 and electrically connected thereto. The imaging cable 38 containing a signal line 114 is connected to the electronic circuit board 114.

Figure 9:
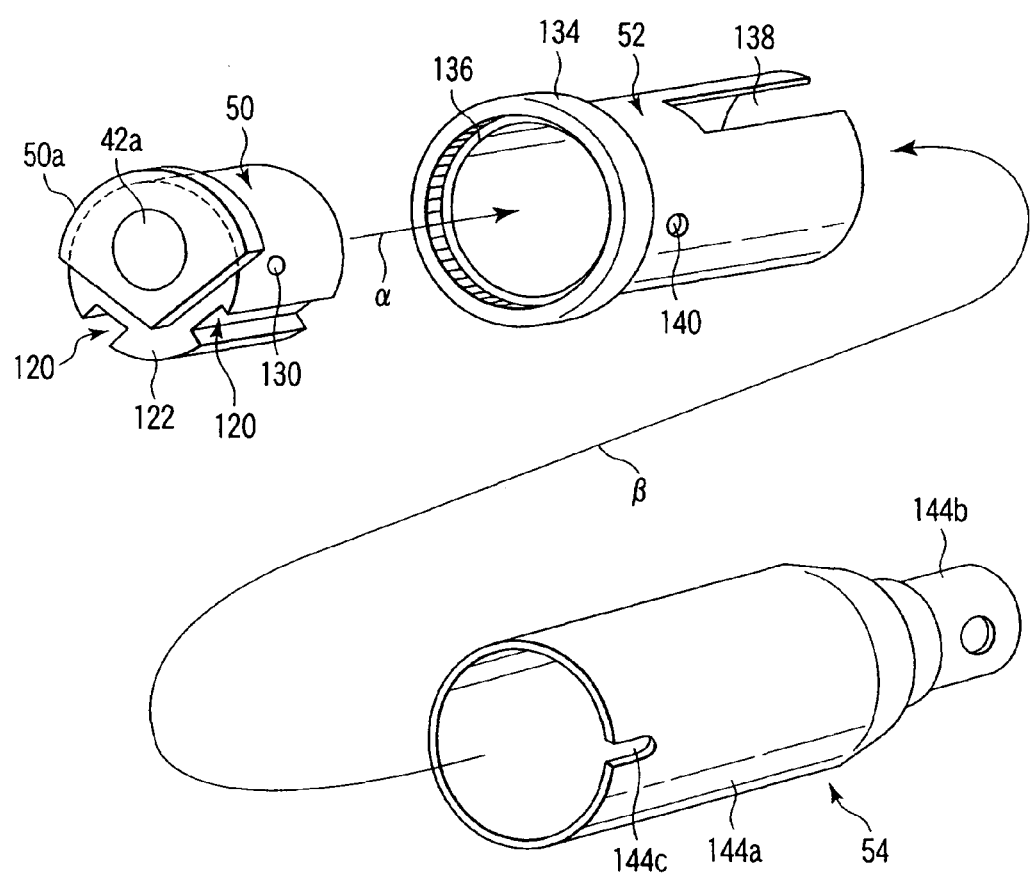
FIG. 9 is an exploded perspective view showing the components constituting the distal-end portion of the insertion section of the endoscope according to the second embodiment.

As FIG. 9 depicts, the basic section of the distal-end portion 8 of the endoscope insertion section 2 includes three parts, i.e., the main body 50, distal-end barrel 52 and cylindrical member 54, as described above. The main body 50 is fitted in the distal-end barrel 52 as arrow a indicates in FIG. 9. The distal-end barrel 52 is fitted in the cylindrical member 54, i.e., outer sheath, as arrow β indicates in FIG. 9.

As FIGS. 8 and 9 show, the main body 50 has a pair of light-guide receptacles 120 made in its outer circumferential surface. The light-guide receptacles 120 are grooves that have a substantially rectangular cross section. The receptacles 120 hold the distal-end portions of the light guides 30, which have a substantially rectangular cross section. Adhesive or the like is applied, securing distal-end portions of the light guides 30 in the light-guide receptacles 120.

The main body 50 has a stepped part 122 at the distal ends of the receptacles 120. The stepped part 122 recedes toward the proximal end of the insertion section 2, from the front of the insertion section 2, which is exposed outside. The illumination windows 32, which are flat glass plates, are fitted in the stepped part 122.

The part of the front of the insertion section 2, other than the stepped part 122, is the flange 50a (see FIG. 7). The flange 50a abuts on the distal end of the distal-end barrel 52 when the barrel 52 is mounted on the main body 50 from the back thereof. The flange 50a therefore serves to position the main body 50.

As FIG. 9 shows, the main body 50 has a positioning hole 130 made in the outer circumferential surface. The hole 130 holds a pin 128 (see FIGS. 10 and 11) that positions the above-mentioned three parts (i.e., main body 50, distal-end barrel 52 and cylindrical member 54).

The distal-end barrel 52 is a thin-walled round tube made of metal. The barrel 52 has a stepped, thick-walled part 134. The thick-walled part 134 has an abutment step 136, on which the flange 50a abuts when the main body 50 is inserted into the distal-end barrel 52. The front of the flange 50a and the front of the distal-end barrel 52 lie in the same plane.

The distal-end barrel 52 has a slit 138 cut in the other end portion and having a prescribed width. As FIG. 7 depicts, the proximal end portion of the main body 50 contains the imaging section 44 that has a larger outer diameter than any other parts of the imaging unit 36. Once the main body 50 has been fitted into the distal-end barrel 52, a part of the imaging section 44 lies between the slit 138, whereby the imaging section 44 is prevented from interfering with the distal-end barrel 52. Thus, the distal-end barrel 52 need not have a larger inner diameter. This imparts a relatively small outer diameter of the insertion section 2.

The distal-end barrel 52 has a hole 140 at prescribed positions. The hole 140 holds the above-mentioned pin 128 (see FIGS. 10 and 11). The pin 128 sets the main body 50 and the distal-end barrel 52 in a specific positional relation.

As seen from FIGS. 7 to 11, the cylindrical member 54 is a thin-walled, metal tube. As FIGS. 7 and 9 show, the cylindrical member 54 has a large-diameter part 144a at the distal end. The large-diameter part 144a has such an inner diameter that it is mounted on the distal-end barrel 52, with no gap between it and the barrel 52. The cylindrical member 54 has a small-diameter part 144b at the proximal end. This part 114 has a smaller diameter than the large-diameter part 144b and has a stepped part.

Figure 10:
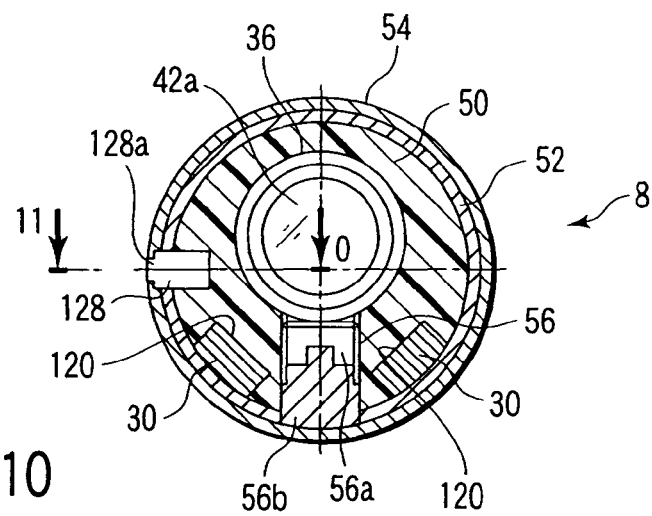
FIG. 10 is a sectional view of the insertion section of the endoscope according to the second embodiment, taken along line 10-10 shown in FIG. 7.
Figure 11:
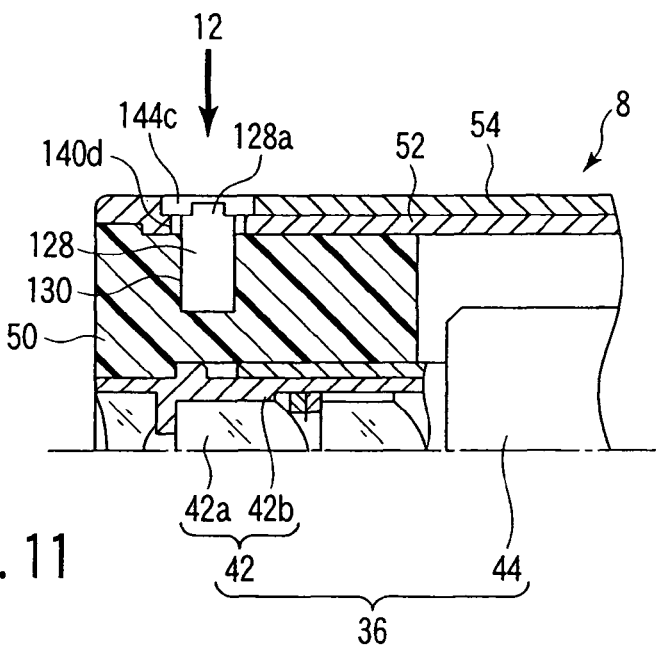
FIG. 11 is a sectional view of the insertion section of the endoscope according to the second embodiment, taken along line 11-0 shown in FIG. 10.

As FIGS. 9 and 11 show, the large-diameter part 144a of the cylindrical member 54 has a slit 144c in the distal-end portion 8. The slit 114c has a width that is substantially equal to the diameter of the small-diameter part 128a of the pin 128 (see FIGS. 10 and 11).

As FIGS. 10 and 11 depict, the small-diameter part 128a of the pin 128 is inserted into the slit 144c of the cylindrical member 54 when the distal-end barrel 52 is fitted into the cylindrical member 54 and the distal end of the member 54 abuts on the stepped part of the distal-end barrel 52 of the distal-end barrel 52. As a result, the distal-end barrel 52 and the cylindrical member 54 are set in a specific positional relation.

Figure 12:
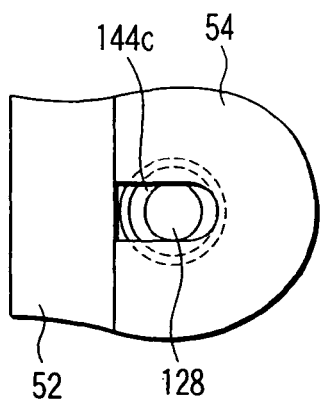
FIG. 12 is a schematic view of a part of the insertion section of the endoscope according to the second embodiment, viewed in the direction of arrow 12 shown in FIG. 11.

That is, as shown in FIGS. 10, 11 and 12, the pin 128 is fitted into the positioning hole 130 of the main body 50 and into the positioning hole 140 of the distal-end barrel 52. Then, the cylindrical member 54 is mounted on the distal-end barrel 52, inserting the small-diameter part 128a of the pint 128 protruding from the outer circumferential surface of the barrel 52, into the slit 144c that has a width substantially equal to the diameter of the small-diameter part 128a of the pin 128. The three distal-end parts mentioned above are thereby positioned with respect to one another, and the pin 128 is held, not slipping out. Now that the pin 128 is so held, the main body 50 is prevented from slipping from the distal-end barrel 52. The distal-end barrel 52 and the cylindrical member 54 contact each other at a large area because that part of the barrel 52 which is fitted in the cylindrical member 54 is relatively long. This insures sufficient adhesion strength between the distal-end barrel 52 and the cylindrical member 54.

Figure 13:
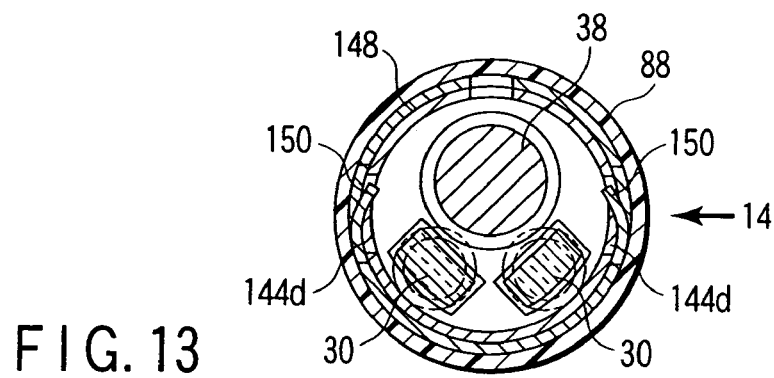
FIG. 13 is a sectional view of he insertion section of the endoscope according to the second embodiment, taken along line 13-13 shown in FIG. 7.
Figure 14:
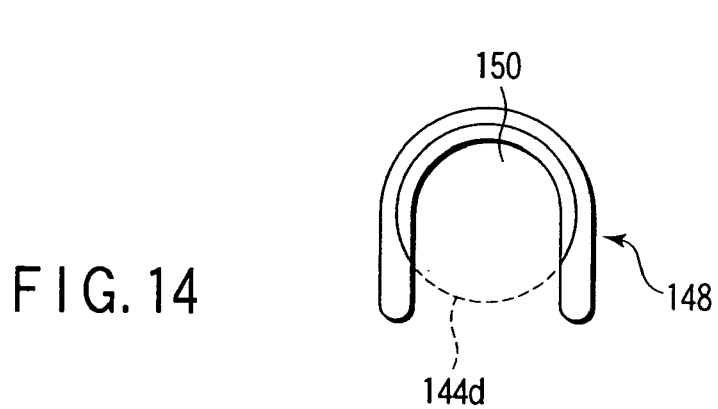
FIG. 14 is a schematic diagram of the insertion section of the endoscope according to the second embodiment, viewed in the direction of arrow 14 shown in FIG. 13.
Figure 15:
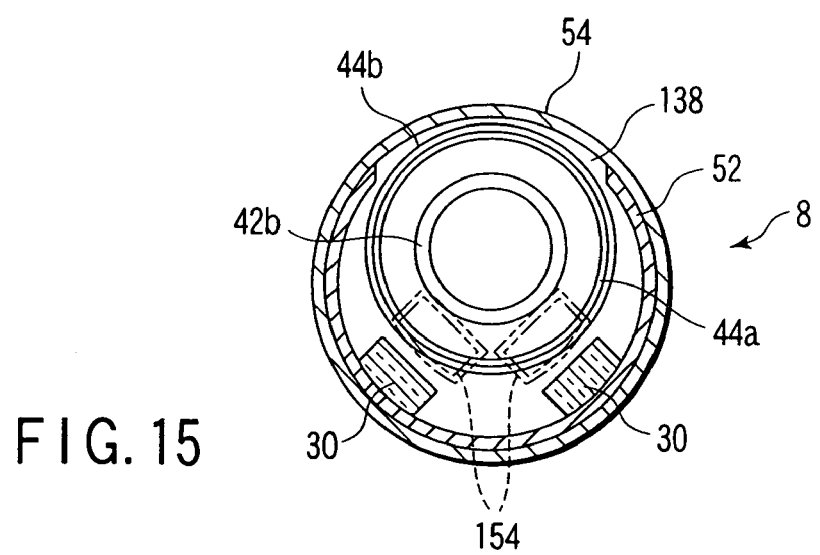
FIG. 15 is a sectional view of the insertion section of the endoscope according to the second embodiment, taken along line 15-15 shown in FIG. 7.

As FIGS. 7 and 9 show, the other end part of the cylindrical member 54 is a stepped, small-diameter part 114b. As illustrated in FIG. 7, an end portion of the most distal one of the annular rings 148 (identical to the annular rings 76 of the first embodiment) that constitute the bending portion 9 of the insertion portion 2 is mounted on the small-diameter part 114b of the cylindrical member 54. The small-diameter part 114b and the end portion of the most distal, annular ring 148 are secured to each other by adhesion. As FIGS. 13 and 14 show, the small-diameter part 114b fitted in the annular ring 148 has caulking holes 114d at prescribed positions. The annular ring 148 has U-slits that may align with the caulking holes 114 when the small-diameter part 114b is fitted into the annular ring 148. The annular ring 148 is therefore provided with tongues 150.

As shown in FIG. 13, the tongues 150 are bent inwards, thus inserted into the caulking holes 144d. Since the tongues 150 are inserted in the caulking holes 144d, the components would not decoupled from each other even if they exfoliate adhering to each other.

The tongues 150 have a tip each. The tip extends toward the circumference of the annular ring 148. Hence, the annular ring 148 is fitted in the cylindrical member 54, overlapping the member 54 for a short distance. As a result, the hard distal-end portion of the annular ring 148 can be short. If the tip of each tongue 150 extended in the longitudinal direction of the insertion portion 2, the tip of each tongue 150 should be long so that its greater part may be bent. In this case, the opening of the annular ring 148 might be deformed if the open end of the body 148 were near the bent parts of the tongues 150, and the annular ring 148 should have a sufficient length.

The distal-end portions of the left and right light guides 30 (of each pair) are fitted tight in the light-guide receptacles 120 are grooves cut in the main body 50 and having a substantially rectangular cross section. More precisely, the light-guide receptacles 120 are spaces defined by the main body 50 and the distal-end barrel 52. Hence, the light guides 30, i.e., bundles of illumination optical fibers, are held tight in the spaces provided between these components.

The illumination light guided through the light guides 30 is applied to the object examined, through the window 32 (see FIG. 7) secured by adhesion in the distal-end portion 8 and fitted in the recess defined by the main body 50 and the distal-end barrel 52.

As FIG. 8 shows, the light guides 30 are fastened to the distal-end portion 8 of the insertion section 2. The insertion section 2 can have a small diameter because the light guides 30 are arranged in the distal-end portion 8, at such a position and in such a space that it does not interfere with the imaging unit 36. Since the light guides 30 have a cross section that is substantially rectangular (particularly, being flat), the dead space in the distal-end portion 8 can be reduced.

As FIG. 8 shows, too, the light guides 30 meander in the form of letter S and extend in the longitudinal direction of the imaging unit 36. Since the light guides 30 are shaped like letter S and extend along the imaging unit 36, they are formed in an increased efficiency. This helps to enhance the efficiency of assembling the light guides 30.

The light guides 30 have their sides secured by adhesion to the inner surface of the distal-end barrel 52, over the entire length of the distal-end barrel 52. Therefore, the filaments of the light guides 30 are hardly broken even if the light guides 30 receive a stress at their bent portions when the light guides are assembled or bent.

To arrange the light guides 30 in the distal-end portion 8, the distal-end portion 8 needs to have passages that have substantially the same shape as the S-shaped portions of the light guides 30. In the present embodiment, spaces defined by the main body 50 and distal-end barrel 52 are used as such passages 154. The passages 154 have a rectangular cross section (or any other cross section other than a circular one) (see FIG. 15).

How the endoscope 1 according to this embodiment is operated will be described, with reference to some drawings.

Assume that a medical treatment is performed on an object, by using, for example, a high-frequency instrument, while observing the object through the endoscope 1 configured as described above.

As FIG. 7 depicts, the main body 50, which is an insulating member, is interposed between the distal-end portion 8 and the imaging section 44 of the imaging unit 36. Hence, high-frequency currents are prevented from leaking to the endoscope 1 through the imaging unit 36 even if the insertion section 2 of the endoscope 1 touches the tissues of the patient. Since the light guide connector 5 and the camera connector 7 electrically insulate the metal sheath of the insertion section 2, no high-frequency currents would leak to the light-source apparatus or the video processor.

As described above, this embodiment is advantageous in the following respects.

The imaging unit 36 can be reliably insulated from the sheath of the insertion section 2. This is because the distal-end part is formed of a plurality of members and the main body 50, i.e., a distal-end member that holds the imaging unit 36, is made of electrically insulating material.

There is no need to cover the distal-end portion of the insertion section 2 or the outer circumferential surface thereof with an insulating sheath. Hence, the rigid part of the distal-end portion 8 can be short, and the outer diameter of the insertion section 2 can be decreased. This renders the endoscope 1 easier to operate.

Insulating parts of high-precision sizes, which are provided in the imaging unit of the conventional endoscope (see Jpn. Pat. Appln. KOKAI Publication No. 2001-46322), need not be used. Therefore, the manufacturing cost of the imaging unit 36 can be reduced, and the assembling of the imaging unit 36 can be simplified.

No insulating members must be interposed between the solid-state imaging element 112 and the lens barrel 42b. Since the element 112 and the barrel 42b can be jointed together with a thin-walled metal frame, the insertion section 2 can have a small diameter.

Of the components of the distal-end part, the distal-end barrel 52 and the cylindrical member 54 are metal pipes. The distal-end part can therefore acquire a sufficient strength.

In order to make the insertion section 2 slender, the space in the distal-end portion 8 must be efficiently used and the light guides 30 having a substantially rectangular cross section (or any other cross section other than a circular one) must be arranged in the distal-end portion 8. However, it is very difficult to make a hole in one part with high precision, in which the light guides are to be held. This inevitably raises the manufacturing cost of this part. In the present embodiment, a hole having a substantially rectangular cross section is made at the junction between two parts. The hole is therefore easy to make. This helps to reduce the manufacturing cost.

In the endoscope 1 according to this embodiment, the insertion section 2 is simple in structure, is composed of few parts and has a small outer diameter. Reliably electrical insulation can yet be achieved between the sheath of the insertion section 2 and the imaging unit 36.

A third embodiment will be described, with reference to FIGS. 16 to 19. The components identical to those of the first and second embodiments are designated at the same reference numerals and will not be described in detail.

As FIG. 16 shows, a first light-guide fiber 212 is arranged in the rigid portion 10 of the insertion section 2. The first light-guide fiber 212 extends to the distal-end portion 8 of the insertion section 2. A second light-guide fiber 214 is arranged in the operation section 3. The second light-guide fiber 214 extends to the light guide connector 5.

In the distal-end portion 8 of the insertion section 2, the first light-guide fiber 212 is secured at distal end to the imaging unit 36 (see FIG. 7).

The first light-guide fiber 212 is a light-guiding element such as an optical fiber. The first light-guide fiber 212 guides illumination light to the window 32 (see FIGS. 3 and 7) secured in the front of the distal-end portion 8. The light is emitted from the window 32 to illuminate the object.

The imaging unit 36 (see FIG. 7) of the insertion section 2 includes an objective-lens system 42 and an imaging section 44. The objective-lens system 42 receives an optical image of the object illuminated with the illumination light and images the image on the solid-state imaging element 112 (see FIG. 7).

The first light-guide fiber 212 is optically connected at proximal end to a light-emitting section (distal-end portion) that can emit the illumination light guided by the second light-guide fiber 214. The light-emitting part of the second light-guide fiber 214 can emit the illumination light to the first light-guide fiber 212 via an optical member 218 (connection mechanism). The optical member 218 performs a light-collecting function and a light-distributing function. Thus, the member 218 collects light in the grip 14 of the operation section 3 and emits the light, and distributes light to the first light-guide fiber 212 and the second light-guide fiber 214.

The second light-guide fiber 214 has the same light-distribution characteristic as the light-guide fibers used in the conventional endoscopes. Therefore, the second light-guide fiber 214 is made of fiber filaments exhibiting light-distribution characteristics fit for use in combination with the light-source apparatuses that are generally used.

The first light-guide fiber 212 is made of fiber filaments that have a greater light-distribution angle than the fiber filaments that constitute the second light-guide fiber 214.

The optical member 218 is arranged between the first light-guide fiber 212 and the second light-guide fiber 214. The light emitted from the distal ends of the second light-guide fiber 214 can therefore be applied to the proximal end of the first light-guide fiber 212. The optical member 218 has, at the light-receiving end, a diameter that is substantially equal to the effective diameter of the first and second light-guide fibers 212 and 214 that abut on the optical member 218.

The optical member 218 is a bundle of fiber filaments, which is shaped like a cone. The conical bundle of fiber filaments is generally known as conical fiber. The conical fiber is characterized in that light emerges from the thin end of the fiber at an angle larger than the angle at which it enters the thick end of the fiber. Hence, the optical member 218 increases the light-distribution angle of the second light-guide fiber 214 to the light-distribution angle of the first light-guide fiber 212.

The optical member 218 is held in a frame member 222 that is shaped like a hollow cylinder. The optical member 218 and the frame member 222 constitute an optical unit 230.

Figure 17:
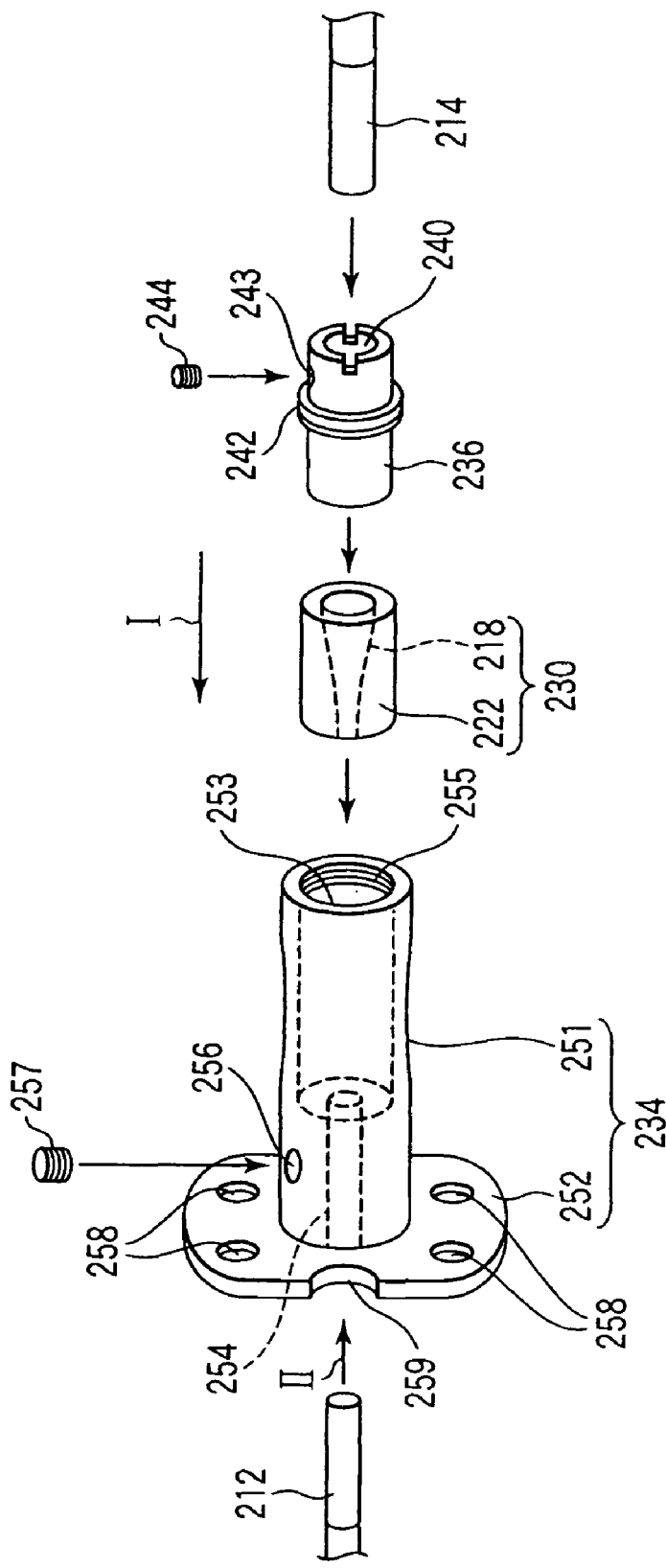
FIG. 17 is an exploded perspective view of the coupling mechanism that couples the first and second light guide fibers provided in the endoscope according to the third embodiment.

As FIGS. 16 and 17 show, the first light-guide fiber 212 has its proximal end fixed to a first cap 234. The second light-guide fiber 214 is secured to a second cap 236. The first and second caps 234 and 236 contain the optical unit 230.

The second cap 236 is shaped like a hollow cylinder. The second cap 236 has a through hole 240 that extends in the axial direction of the second cap 236. A male screw 242 is cut in the outer circumferential surface of the second cap 236. The second cap 236 has a screw hole 243 in a part that is close to the light guide connector 5. The screw hole 243 extends from the outer circumference of the second cap 236 to the inner circumference thereof. A screw 244 is driven in the screw hole 243, holding the second light-guide fiber 214 to the second cap 236.

The second light-guide fiber 214 extends from the light guide connector 5 into the grip 14 through the universal cable 4. The distal end of the second light-guide fiber 214 is inserted into the hole 240 made in the second cap 236 and is held steadfast in the hole 240 by the screw 244 driven in the screw hole 243.

The fist cap 234 includes a main body 251 and a flange 252. The main body 251 is shaped like a hollow cylinder. The flange 252 is a disc that is formed integral with one end of the main body 251. The main body 251 of the first cap 234 has a large-diameter opening 253 in the side that faces the connector 5. A female screw 255 is cut in the inner surface of the opening 253, near the rim of the opening 253. The main body 251 has a small-diameter opening 254 in the side that faces the insertion section 2.

The optical unit 230, which is a light-distribution adjusting means shaped like a hollow cylinder, is inserted into the large-diameter opening 253. The male screw 242 of the second cap 236 is set in screw engagement with the female screw 255 of the first cap 234. The optical unit 230 is therefore pushed into that part of the first cap 234 that faces the distal-end portion 8 of the insertion section 2.

The step of securing the second light-guide fiber 214 to the second cap 236 is carried out after the second cap 236 has been set into screw engagement with the first cap 234.

First, the second light-guide fiber 214, second cap 236 and optical unit 230 are arranged with respect to the first cap 234 in the direction of arrow I shown in FIG. 17, one after another in the order they are mentioned.

The first cap 234 has a screw hole 256 in the part that is close to the distal-end portion 8 of the insertion section 2. The screw hole 256 extends from the outer circumference of the first cap 234 to the inner circumference thereof. A screw 257 is driven in this screw hole 256, holding the first light-guide fiber 212.

The first light-guide fiber 212 inserted into the grip 14 through the distal-end portion 8 has its proximal end inserted in the opening 254 of the first cap 234 and secured by the screw 257. The first light-guide fiber 212 abuts at the proximal end on the optical member 218. The second light-guide fibers 214 abut at the distal end, on the optical member 218.

Thus, the first light-guide fiber 212 is arranged with respect to the first cap 234, extending in the direction of arrow II shown in FIG. 17.

As is illustrated in FIG. 16, screws fasten inner coupling plates 262 to a receptacle cylinder 261 that is mechanically fixed to the operation section 3. To the distal ends of the inner coupling plates 262, a hollow cylindrical body 263 holding the light-guide fibers is secured by screws. The first cap 234 is secured at its flange 252 to the hollow cylindrical body 263 by means of screws.

At the interfaces between the optical member 218 and the first and second light-guide fibers 212 and 214, both held in the cap 234, heat is generated due to the transmission loss of the illumination light. The heat does not directly propagate to the outer surface of the grip 14, nevertheless. This is because a layer of air is formed between the outer circumferential surface of the first cap 234 and either inner coupling plate 262. The internal components, such as first cap 234, hollow cylindrical body 263 holding the light-guide fibers, inner coupling plates 262 and receptacle cylinder 261, are made of materials of high thermal conductivity. Hence, they can diffuse heat well.

As FIGS. 17 and 18 show, the flange 252 of the first cap 234 has wire-guiding holes 258. Wires 66 for bending the bending portion 9 (FIG. 1) extend through the wire-guiding holes 258. The flange 252 has a notch 259. The imaging cable 38 passes through this notch 239, extending from the distal-end portion 8 and passing through the insertion section 2.

A light-guide fiber receptacle 271 is provided in the hollow cylindrical body 263 to which the first cap 234 is secured. As FIG. 19 shows, the light-guide fiber receptacle 271 is a cylindrical hollow that has a radius R larger than the radius of curvature of the first light-guide fiber 212. As FIG. 16 depicts, that part of the first light-guide fiber 212, which lies in this cylindrical hollow, has a helical shape. The helical part of the first light-guide fiber 212, which exists in the light-guide fiber receptacle 271, has a bent portion 272.

As shown in FIG. 19, the cylindrical body 263 holding the light-guide fibers has two openings 265 that diametrically oppose each other. These openings 265 make it easy to lay the first light-guide fiber 212 in a helical shape.

As FIG. 16 depicts, that portion of the first light-guide fiber 212, which is closer to the distal-end portion 8 than the bent portion, is inserted in the passage 273 made in the rigid portion 10 of the insertion section 2. The distal-end portion 8 and the bending portion 9 shown in have a passage 273, too, in which the first light-guide fiber 212 is inserted.

The second light-guide fiber 214, optical member 218 and first light-guide fiber 212 guide the illumination light emitted from the light-source apparatus (not shown), to the distal end of the insertion section 2. Thus, the light is applied through the illumination windows 32 (see FIGS. 3 and 7) at desired angles of incidence, illuminating the object.

As described above, the second light-guide fiber 214 has a light-emitting part (distal part) that can emit the illumination light coming from the light source apparatus.

Functioning as connecting mechanism, the optical member 218 optically connects the first light-guide fiber 212 to the second light-guide fiber 214. The first light-guide fiber 212 can therefore receive the illumination light emitted from the light-emitting part of the second light-guide fiber 214.

As indicated above, the insertion section 2 has a passage 273. Through the passage 273, the first light-guide fiber 212 extends from the proximal end of the insertion section 2 to the distal end thereof.

The light-guide fiber receptacle 271 communicates with the proximal end of the passage 273 and has a larger diameter than the passage 273. The distal end part of the light-guide fiber receptacle 271 can accommodate at least one portion of the proximal part of the first light-guide fiber 212, which is held in the passage 273.

The bent portion 272 of the first light-guide fiber 212 is held in the light-guide fiber receptacle 271.

The connection mechanism (optical member 218) is secured in the operation section 3 of the endoscope 1.

This mechanism has a frame member 222, in addition to the first cap 234 and the second cap 236. The frame member 222 holds the first light-guide fiber 212 and the second light-guide fiber 214 that are connected to an outer component such as the grip 14 provided on the operation section 3 of the endoscope 1.

The optical member 218, which is used as light-collecting means, optically connects the first light-guide fiber 212 and the second light-guide fiber 214.

The first light-guide fiber 212 and the second light-guide fiber 214 differ in terms of light-distribution angle. Thus, they are connected by the optical member 218 that changes the light-distribution angle of one light-guide fiber to that of the other light-guide fiber.

How the endoscope 1 according to this embodiment is operated will be described below.

The operator fastens the first light-guide fiber 212 to the first cap 234 provided in the grip 14 before inserting the fiber 212 into the insertion section 2, bending the fiber 212 in the form of a spiral, thus forming a bent portion 272, which is held in the cylindrical body 263. At this time, the density at which the fiber 212 are arranged in the cylindrical body 263 is adjusted, utilizing the excessive part of the first light-guide fiber 212.

The second light-guide fiber 214 that extends through the universal cable 4 is secured at distal end to the first cap 234. The excessive part of the second light-guide fiber 214 is laid in the light guide connector 5.

The illumination light that is required in observing the object through the endoscope is applied from the light source apparatus to the proximal end of the second light-guide fiber 214 and emerges from the distal end of the fiber 214. The illumination light is then guided to the optical member 218 provided in the grip 14. The illumination light thus applied to the optical member 218 has its light-distribution angle changed. The light can therefore enter the proximal end of the first light-guide fiber 212 at high efficiency. The illumination light propagates through the first light-guide fiber 212 and emerges from the distal end of the first light-guide fiber 212. The illumination light is then applied through the illumination windows 23 to a position in front of the distal-end portion 8 of the insertion section 2. Thus, the light illuminates the object that exists in front of the distal-end portion 8 of the insertion section 2.

At this time, the heat resulting from a loss of light occurring between the first and second light-guide fibers 212 and 214 propagates from the first cap 234 to the cylindrical body 263 and the inner coupling plates 262. The heat is then distributed to the other inner components.

From the foregoing, the following can be said of the endoscope 1 according to this embodiment.

As indicated above, the coupling members (i.e., frame member 222, first cap 234 and second cap 236) connecting the first and second light-guide fibers 212 and 214, and the optical member 218 interposed between the light-guide fibers 212 and 214 are reliably secured in the operation section 3 of the endoscope 1. Hence, the coupling members would not move even if the endoscope 1 receives an impact from outside while being used or transported. This reliably prevents the first and second light-guide fibers 212 and 214 from being damaged even if the operation section 3 receives an impact, thanks to the inertia of the coupling members. Thus, a load is exerted on neither the first light-guide fiber 212 nor the second light-guide fiber 214. The filaments of the first and second light-guide fibers 212 and 214 would not be broken.

The first light-guide fiber 212 is laid in a helical (coil) shape, within a space (i.e., light-guide fiber receptacle 271) having a radius larger than the radius of curvature of the first light-guide fiber 212 that is bent most. In addition, the excessive part of the first light-guide fiber 212 can be adjusted in length by changing the density of coil turns (condensation or rarefaction). Thus, much room is available for the excessive part of the first light-guide fiber 212. In other words, a large space is provided to accommodate the excessive part of the first light-guide fiber 212. This helps to enhance the efficiency of laying the light-guide fiber 212 in the endoscope 1.

The first light-guide fiber 212 need not be restricted in terms of length; it can be somewhat shorter or longer than the design length. This makes it easy to process the first light-guide fiber 212. Further, the filaments of the first light-guide fiber 212 are prevented from being broken when the fiber 212 is incorporated into the endoscope 1.

An air layer is provided around the coupling members (i.e., frame member 222, first cap 234 and second cap 236) connecting the first and second light-guide fibers 212 and 214. The coupling members are arranged and fixed, not contacting the outer sheath (i.e., grip 14) of the operation section 3. The outer sheath is therefore prevented from being heated, not annoying the surgeon who is using the endoscope 1. The coupling members are made of material of high thermal conductivity. So are the inner components that secure the coupling members. Heat can therefore be dispersed well. Heat will not accumulate in the operation section 3 of the endoscope 1 even if the endoscope 1 is used for a long time.

Thus, no damages would be done to the light-guide fibers 212 and 214, thanks to the inertia of the coupling members, even if the operation section 3 receives an impact. A load is hardly applied to the light-guide fibers. The filaments of the light-guide fibers 212 and 214 would not be broken in the operation section 3. Since the excessive parts of the light-guide fibers 212 and 214 are loosely laid in the operation section 3, the fibers 212 and 214 can have a large allowance of length. This helps to enhance the efficiency of processing the light-guide fibers 212 and 214 and can prevent the filaments of either light-guide fiber from being broken when the fiber is incorporated into the endoscope 1.

Some embodiments of this invention have been described, with reference to the accompanying drawings. Nonetheless, the present invention is not limited to these embodiments. The invention includes any embodiments that are possible without departing the scope and spirit of the invention.

What is claimed is:

1. An endoscope comprising:
an insertion section including:
an endoscope distal-end portion;
a bending portion disposed on a proximal end of the endoscope distal-end portion and including an annular ring assembly having a plurality of annular rings capable of flexing respectively about an axial direction of the insertion section; and
an entirely hard tubular body which is disposed on a proximal end of the bending portion and which is configured to prevent deformity and to maintain the shape thereof when the hard tubular body is subjected to external force;

at least one first inner component having a distal end and a proximal end, the distal end of the first inner component being secured at the endoscope distal-end portion and the first inner component passing through the bending portion and the hard tubular body; and at least one second inner component having a distal end and a proximal end, the second inner component has the same or greater flexibility than the first inner component, the second inner component passing through the bending portion and the hard tubular body and the distal end of the second inner component being secured at a position more peripherally located as compared to a more central location of the first inner component at the endoscope distal-end portion;

wherein:

(a) the annular rings of the annular ring assembly are rotatable relative to each other;

(b) each annular ring includes:

(i) at least a pair of through holes through which wires for bending the bending portion pass through; and (ii) a plurality of partitions which protrude radially inward towards a center of the annular ring, and the through holes being formed in the partitions; and (iii) a pair of bulging portions at one end face thereof, which are configured as fulcrums for an adjacent annular ring, configured to be disposed on the partition, respectively, and the through holes being formed in the bulging portions, wherein an outer side surface of the bulging portions opposite a side of the center of the annular ring coincides with an outer peripheral surface opposite the side of the center of the annular ring, a first inner component storage portion defined within an imaginary circle which tangentially contacts apexes of the partitions, the storage portion serving to hold the first inner component; and a second component storage portion defined between adjacent pairs of the partitions and serving to hold the second inner component and (c) the insertion section being configured such that when the annular ring assembly receives twisting force about the axial direction of the insertion section, all annular rings rotate sequentially toward the proximal end of the bending portion about the axial direction of the insertion section, the partitions provided in each annular ring, move about the axial direction of the insertion section, describing loci that are substantially spiral, and the first inner component being configured to move and be stored within the imaginary circle as the second inner component being twisted as the second inner component moves through spiral paths defined by the partitions.

2. The endoscope according to claim 1, wherein the first inner component comprise one of an imaging cable and a forceps channel, and the second inner component comprises one of a light guide and an image guide fiber.

3. The endoscope according to claim 1, wherein the hard tubular body is formed of a hard metal.

4. The endoscope according to claim 1, wherein the hard tubular body is formed of stainless steel.

5. The endoscope according to claim 1, wherein an axial end face of each said bulging portion is configured to support an adjacent one of said annular rings as a fulcrum.

6. The endoscope according to claim 1, wherein the through holes formed in the bulging portions extend to an axial end face of said bulging portions.

* * * * *